(12) United States Patent
Coe et al.

(10) Patent No.: US 6,179,970 B1
(45) Date of Patent: Jan. 30, 2001

(54) PROCESS FOR THE PREPARATION OF FLUORO COMPOUNDS FROM THE CORRESPONDING AMINES

(75) Inventors: Paul Coe; Tony Waring, both of Birmingham; Claude Mercier, Bristol, all of (GB)

(73) Assignee: Rhodia Limited, Hertfordshire (GB)

( * ) Notice: Under 35 U.S.C. 154(b), the term of this patent shall be extended for 0 days.

(21) Appl. No.: 09/180,015

(22) PCT Filed: May 1, 1997

(86) PCT No.: PCT/GB97/01201

§ 371 Date: Apr. 7, 1999

§ 102(e) Date: Apr. 7, 1999

(87) PCT Pub. No.: WO97/41083

PCT Pub. Date: Nov. 6, 1997

(30) Foreign Application Priority Data

May 1, 1996 (GB) .................................................. 9609154

(51) Int. Cl.⁷ ............................. C01B 7/00; C07C 17/00
(52) U.S. Cl. ................................ 204/157.62; 204/157.42; 204/157.43; 204/157.48; 204/157.94; 204/157.99; 204/158.11
(58) Field of Search ......................... 204/157.42, 157.43, 204/157.48, 157.62, 157.94, 157.99, 158.11

(56) References Cited

U.S. PATENT DOCUMENTS

| 3,481,850 | 12/1969 | Petterson et al. | 204/163 |
| 5,354,439 | * 10/1994 | Forat et al. | 204/157.6 |

FOREIGN PATENT DOCUMENTS

| 141750 | 10/1930 | (CH) . |
| 0 430 434 A2 | 6/1991 | (EP) . |
| 0 467 742 A1 | 1/1992 | (EP) . |

OTHER PUBLICATIONS

N. Yoneda et al., "Preparation of Aromatic Fluorides by Photochemical Diazotization and Decomposition of Aromatic Amines", Chemical Abstracts, 110(3):23510v (1989) no month available.

Müeller et al., "Ultraschallforcierte Balz–Schiemann–Reaktion Unter Thermisch Milden Bedingungen", Z. Chem. 26, pp. 169–170 (1986) no month available.

* cited by examiner

Primary Examiner—Kathryn Gorgos
Assistant Examiner—Edna Wong
(74) Attorney, Agent, or Firm—Finnegan, Henderson, Farabow, Garrett & Dunner, L.L.P.

(57) ABSTRACT

Compounds containing a primary amino group are converted into compounds containing a fluorine atom in place of the amino group by reaction of the amino compound with hydrogen fluoride and a nitrosating reagent under the influence of ultrasound or microwaves.

8 Claims, No Drawings

PROCESS FOR THE PREPARATION OF FLUORO COMPOUNDS FROM THE CORRESPONDING AMINES

This is a national stage application of PCT/GB97/01201, filed May 1, 1997.

This invention relates to the preparation of fluoro compounds from amines by replacement of the amino group by a fluorine atom.

It is known to produce fluoro compounds from corresponding amines, particularly aromatic amines, by conversion of the latter into a diazonium tetrafluoroborate salt which is then decomposed thermally to produce the fluoro compound. It is also known to carry out the diazotization of aromatic amines in anhydrous hydrofluoric acid with subsequent heating to produce the corresponding fluoro compound. Neither of these methods is entirely satisfactory. The first involves isolation of the tetrafluoroborate salt which is hazardous and time consuming. The latter method gives poor yields when substituted aromatic amines are used, especially if the substitution is in the ortho position. Also, the reaction has to be carried out under pressure because anhydrous hydrofluoric acid is volatile.

There have been a number of proposals of methods for the production of fluoro compounds which are said to give improved results. For example, European Specification EP-A-0430434 (Imperial Chemical Industries plc.) describes a process for the preparation of fluoro aromatic and fluoro heteroaromatic compounds by reaction of corresponding aromatic or heteroaromatic amines with a nitrosyl polyfluoro salt in an inert liquid followed by decomposition of the diazonium polyfluoro salt obtained in situ. It has also been proposed (Müeller et al Z. Chem. 26 (1986) pp 169–170) to bring about the decomposition of aromatic diazonium fluoroborates in a fluorinated hydrocarbon reaction medium in the presence of $Et_3N.3HF$ under the influence of ultrasound at 40° C. It is stated that high yields may be obtained. However, this method like other known methods involving the use of diazonium tetrafluoroborates, requires isolation of the tetrafluoroborate salt.

It has now been found that compounds containing a primary amino group can be converted into compounds containing a fluorine atom in place of the amino group without isolation of any intermediate diazonium salt and with excellent yields of the desired product, if the reaction is carried out with ultrasound.

The present invention accordingly provides a process for converting a compound containing a primary amino group into a compound containing a fluorine atom in place of the said amino group which comprises contacting the said amino group containing compound with hydrogen fluoride, or with a complex thereof with a base, and with a nitrosating agent, at a temperature in the range of −20° to +100° C. while the reagents are subjected to the action of ultrasound having a frequency of 10–100 kHz and an intensity of at least 20 watts/cm² and/or microwaves having a frequency of 300 MHz to 3 GHz and an intensity of 100 W to 5 kW.

This process is applicable to a wide variety of amino group containing compounds including more particularly aromatic and heteroaromatic primary amines and alpha-amino acids.

The invention may be, for example, applied to aromatic amino-compounds of the formula $$A(NH_2)_n$$

where A is an unsubstituted or substituted aromatic or heteroaromatic radical and n is an integer, e.g. from 1 to 4.

A may be for example a residue of benzene, naphthalene, diphenyl, acetonaphthene, fluorene, or pyrene or a heteroaromatic compound such as pyridine or quinoline.

The invention may also be applied to α-amino acids such as alanine, valine, phenylalanine, isoleucine, tyrosine, and threonine, and to aralkylamines such as phenylethylamine.

Examples of suitable aromatic and heteroaromatic amines which may be subjected to the process of the present invention may be represented by the general formula:

where Ar is phenyl, α- or β-naphthyl, pyridyl, quinolyl, thienyl, or diphenyl, n is 0, 1, 2 or 3 and R is halogen, alkyl, hydroxy, alkoxy, COOH, CHO, alkoxycarbonyl, nitro, cyano, trifluoromethyl, carbamoyl, alkylcarbamoyl, dialkylcarbamoyl, sulphonamido, alkanoyl, or aroyl.

Preferred aromatic primary amines which may be used in the process of the invention conform to the general formula:

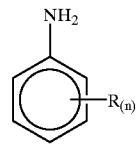

where n is 0, 1, 2 or 3 and the radicals R, which may be the same or different when n is 2 or 3, are each halogen, e.g. fluorine or chlorine, alkyl of 1 to 4 carbon atoms, e.g. methyl or ethyl, hydroxy, alkoxy of 1 to 4 carbon atoms, e.g. methoxy or ethoxy, alkylthio of 1 to 4 carbon atoms, e.g. methylthio, carboxy, alkoxycarbonyl with 1 to 4 carbon atoms in the alkoxy, nitro, cyano or trifluoromethyl.

The hydrogen fluoride is preferably introduced into the reaction mixture in the form of a complex with a base which is preferably a secondary or tertiary aliphatic amine, a heterocyclic aromatic amine, or an ether. Examples of suitable compounds are triethylamine, diisopropylamine, pyridine, tetrahydrofuran, diethyleneglycol dimethyl ether, 1,3-dioxolane, and dioxane.

The nitrosating reagent is preferably an alkali metal nitrite, e.g. sodium nitrite, or a nitrite ester, e.g. ethyl nitrite. It is also possible to use other nitrosating agents, for example nitrosyl fluoroborate or nitrogen oxides.

In some cases improved yields are obtained by incorporating boron trifluoride etherate into the reaction mixture.

The amount of nitrosating reagent which is used in the process can be varied within wide limits. Preferably from 1.0 to 5.0, especially from 1.0 to 2.0 and more especially from 1.1 to 1.5, mole of nitrosating reagent is used per mole of primary amine.

The amount of hydrogen fluoride complex to primary amine can be carried within wide limits. Preferably 5 to 200, especially 10 to 50 and more especially 10 to 25, parts of liquid are used per part of primary amine.

The reaction may be carried out at any temperature in the range −20° C. to +150° C., but it is preferably carried out at 0 to 70° C., and especially at 0 to 50° C. The pressure is not critical and it is ordinarily convenient to carry out the reaction at ambient pressure.

The ultrasound or microwaves may be provided using commercially available sources, e.g. an ultrasonic cleaning bath or a microwave oven. The frequency of the ultrasound should be chosen to maximise absorption of energy by the reaction medium. Typically, the ultrasound should have an intensity of at least 20, preferably 50, more preferably 100 and especially 200 W/cm$^2$. Microwaves should have a frequency of 300 MHz to 3GHz and a power of 200 W to 5 kw. (In some countries, the maximum frequency is fixed by law.)

Following completion of the reaction (shown by disappearance of the starting amine and the intermediate diazonium salt from the reaction medium) the desired fluoro compound may be worked up in the usual way.

The fluoro compounds obtained are useful as intermediates in the manufacture of a wide range of products including pharmaceuticals, herbicides, pesticides, dyestuffs and plastics.

The following Examples illustrate the invention.

EXAMPLE 1

Diazotization of 2,4,6-trimethylaniline in Et$_3$N-3HF 2,4,6-Trimethylaniline (2.3 g, 0.02 mol) was syringed over a period of 30 minutes into Et$_3$N-3HF (30 cm$^3$) at 0° C. in a 100 cm$^3$ 3-necked glass flask, which had been placed in an operating ultrasonic bath (type T460/H (285 watts). The addition of sodium nitrite (2.0 g, 0.03 mol) in 200 mg portions at 0° C. caused the reaction mixture to turn initially to a yellow colour which progressively darkened. Very little tar was formed during the reaction. The mixture was then allowed to warm to room temperature and was exposed to ultrasound for 20 minutes more. The reaction mixture had now turned brown and very little undissolved sodium nitrite could be seen in the solution. The mixture was poured into water (150 cm$^3$) and the product extracted with diethyl ether (200 cm$^3$) and dried over magnesium sulphate.

Following fractional distillation to remove the diethyl ether a red oil was isolated, which was distilled at 150–153° C. @ atmospheric pressure. The distillation was complete in 45 minutes affording 1-fluoro-2,4,6-trimethylbenzene (2.1 g, 89.3%) as a colourless liquid.

The $^1$H n.m.r. spectrum contained signals at $\delta_H$ (CDCl$_3$) 2.31, 2-CH$_3$ and 6-CH$_3$ (d, J=2.0 Hz, 6H); 2.32, 4-CH$_3$ (s, 3H); 6.88, 3-H and 5-H (d, J=7.0 Hz, 2H). The $^{19}$F n.m.r. spectrum had a signal at $\delta_F$ (CDCl$_3$) 127.8, 1-F (s).

The mass spectrum produced a molecular ion at m/z 138 and the expected fragmentation pattern for 1-fluoro-2,4,6-trimethylbenzene at m/z 123, 109, 97, 91 and 83.

EXAMPLE 2

Diazotization of 2,6-dimethylaniline in Et$_3$N-3HF

The diazotization of 2,6-dimethylaniline (2.3 g, 0.02 mol) was performed under the same conditions as described for 2,4,6-trimethylaniline in Example 1. The reaction mixture turned yellow during the initial addition of sodium nitrite (2.0 g, 0.03 mol) and gradually turned red with the increased addition of sodium nitrite. Some tar was formed which was easily extracted with solvent. The work-up was identical to that described for 2,4,6-trimethylaniline. Diethyl ether (150 cm$^3$) was used for the extraction of the organic layer from the aqueous washings. The organic extract was dried over magnesium sulphate.

Fractional distillation of the solvent formed an orange oil which was distilled at 141–143° C. @ atmospheric pressure affording 1-fluoro-2,6-dimethylbenzene (2.0 g, 86.3%) as a colourless liquid. The distillation was complete in 1 hour.

The $^1$H n.m.r. spectrum contained signals at $\delta_H$ (CDCl$_3$) 2.25, 2-CH$_3$ and 6-CH$_3$ (d, J=2.0 Hz, 6H); 6.91, 3-H and 5-H (dd, J=8.3 Hz and J=6.5 Hz, 2H) and 7.01, 4-H (t, J=8.0 Hz, 1H). The $^{19}$F n.m.r. spectrum had a signal at $\delta_F$ (CDCl$_3$) 122.5, 1-F (ts, J=6.5 Hz and J=2.0 Hz).

The mass spectrum produced a molecular ion at m/z 124 and the expected fragmentation pattern for 1-fluoro-2,6-dimethylbenzene at m/z 109, 103, 96, 89, 83 and 77.

EXAMPLE 3

Diazotization of 2,5-dimethylaniline in Et$_3$N-3HF 2,5-Dimethylaniline (2.3 g, 0.02 mol) was syringed into Et$_3$N-3HF (30 cm$^3$) over a 35 minute period. The reaction mixture turned red during the addition of sodium nitrite (2.0 g, 0.03 mol) and a significant amount of nitrogen was evolved during the reaction. Although a high proportion of sodium nitrite was seen to dissolve a greater proportion of tarry material was formed. The mixture was poured into water (150 cm$^3$) and the remaining contents of the flask washed with further water (30 cm$^3$×2). The mixture was extracted with diethyl ether (150 cm$^3$×2) and the organic layer dried over magnesium sulphate.

Fractional removal of diethyl ether afforded an orange oil. Distillation of the oil at 144–146° C. @ atmospheric pressure afforded 1-fluoro-2,5-dimethylbenzene (1.52 g, 65.5%) as a clear colourless liquid.

The $^{19}$F n.m.r. spectrum had a signal at $\delta_F$ (CDCl$_3$) 121.9, 1-F (ddq, J=8.5 Hz, J=10.5 Hz and J=2.2 Hz). From the GC/MS the compound showed the expected molecular ion at m/z 124 and the expected fragmentation for 1-fluoro-2,5-dimethylbenzene at m/z 109, 101, 96, 83 and 77.

EXAMPLE 4

Diazotization of 2,4-dimethylaniline in Et$_3$N-3HF

A similar approach was used for the diazotization of 2,4-dimethylaniline as that described in Example 1. Addition of sodium nitrite (2.0 g, 0.03 mol) to 2,4-dimethylaniline (2.3 g, 0.02 mol), initially formed a yellow colour which eventually turned orange. Diazotization became evident after 20 minutes when the evolution of gas was vigorous. Very little undissolved sodium nitrite was detected at the end of the reaction.

Work-up as described in Example 1 for 2,4,6-trimethylaniline formed a brown oil on distillation of diethyl ether. Distillation of the oil at 143–144° C. @ atmospheric pressure afforded 1-fluoro-2,4-dimethylbenzene (1.73 g, 74.6%) as a clear liquid.

The $^1$H n.m.r. spectrum contained signals at $\delta_H$ (CDCl$_3$) 2.23, 2-CH$_3$ (d, J=1.8 Hz, 3H); 2.28, 4-CH$_3$ (s, 3H); 6.87, 6-H (t, J=9.0 Hz, 1H); 6.92, 5-H (ddd, J=8.0 Hz, J=5.5 Hz and J=2.0 Hz, 1H) and 6.97, 3-H (dm, J=7.8 Hz and J=2.0 Hz, 1H). The $^{19}$F n.m.r. spectrum has a signal at $\delta_F$ (CDCl$_3$) 124.2, 1-F (complex m).

The mass spectrum produced a molecular ion at m/z 124 and the expected fragmentation pattern for 1-fluoro-2,4-dimethylbenzene at m/z 109, 101, 96, 89, 83 and 77.

EXAMPLE 5

Diazotization of 2,3-dimethylaniline in Et$_3$N-3HF 2,3-Dimethylaniline (2.3 g, 0.02 mol) was syringed into Et$_3$N-3HF (30 cm$^3$) at 0° C. The addition of sodium nitrite (2.0 g, 0.03 mol) caused the evolution of gas under the influence of ultrasound, which was significant during the first 25 minutes. The clear reaction mixture gradually turned yellow and progressively darkened with the formation of tar. The brown mixture was poured into water (150 cm$^3$) and extracted with diethyl ether (180 cm$^3$×2). The remaining tarry residue was transferred to a Soxhlet apparatus and extracted repeatedly with diethyl ether (30 cm$^3$) over 24 hours. The ether extracts were dried over magnesium sulphate and fractional removal of diethyl ether afforded a brown oil.

Distillation of the oil at 142–143° C. @ atmospheric pressure afforded 1-fluoro-2,3-dimethylbenzene (1.47 g, 63.4%) as a clear liquid.

The $^1$H n.m.r. spectrum had signals at $\delta_H$ (CDCl$_3$) 2.18, 2-CH$_3$ (d, J=2.0 Hz, 3H); 2.28, 3-CH$_3$ (s, 3H); 6.88, 6-H (t, J=7.6 Hz, 1H) and 6.91, 4-H (d, J=7.6 Hz, 1H) and 7.03, 5-H (q, J=8.0 Hz and J=6.0 Hz, 1H). The $^{19}$F n.m.r. spectrum had a signal at $\delta_F$ (CDCl$_3$) 118.3, 1-F (tq, J=7.6 Hz and J=2.0 Hz).

The mass spectrum produced a molecular ion at m/z 124 and the expected fragmentation pattern for 1-fluoro-2,3-dimethylbenzene at m/z 109, 101, 96, 86, 83 and 77.

EXAMPLE 6

Diazotization of 3,4-dimethylaniline in Et$_3$N-3HF 3,4-Dimethylaniline (2.3 g, 0.02 mol) was added to Et$_3$N-3HF in proportions (0.15 g) over a 40 minute period at 0° C. Sodium nitrite (2.3 g, 0.03 mol) was added in small quantities (100 mg) under the influence of ultrasound. The slow addition of both substrates helped to reduce the formation of tar. After the complete addition of both substrates, the reaction vessel was allowed to warm to room temperature and ultrasound was applied for a further 10 minutes. The mixture was poured into water (100 cm$^3$). The organic layer was extracted with diethyl ether (150 cm$^3$×2) and dried over magnesium sulphate.

Fractional distillation of the solvent afforded a brown oil which was distilled at 138–139° C. @ atmospheric pressure affording 1-fluoro-3,4-dimethylbenzene (1.30 g, 56.1%) as a clear liquid. Attempts were made to extract any material with a Soxhlet apparatus, but such measures did not improve the isolated yield of the product. The $^{19}$F n.m.r. spectrum had a signal at $\delta_F$ (CDCl$_3$) 120.1, 1-F (dddq, J=6.0 Hz, J=9.6 Hz, J=8.6 Hz and J=1.0 Hz). From the GC/MS the compound showed the expected molecular ion at m/z 124 and the expected fragmentation for 1-fluoro-3,4-dimethylbenzene at m/z 109, 101, 97, 83 and 77.

EXAMPLE 7

Diazotization of 4-fluoroaniline in Et$_3$N-3HF

4-Fluoroaniline (2.3 g, 0.02 mol) was syringed over a period of 25 minutes into Et$_3$N-3HF at 0° C. under the influence of ultrasound. The addition of sodium nitrite (2.0 g, 0.03 mol) in 150 mg portions caused the reaction mixture to adopt an orange colour which progressively darkened with the formation of a small quantity of tar. During the initial addition of sodium nitrite there was evolution of gas. The mixture was then allowed to warm to ambient temperature and exposed to ultrasound for a further 25 minutes. The reaction contents were poured into water and the organic constituents were extracted with diethyl ether (200 cm$^3$). The ether extract was dried over magnesium sulphate and fractional distillation of solvent afforded a brown oil.

Distillation of the oil at 88–90° C. @ atmospheric pressure afforded 1,4-difluorobenzene (1.49 g, 63.1%) as a clear liquid. The i.r. spectrum contained major peaks at $\upsilon_{max}$ 3079 cm$^{-1}$ ($\upsilon_{ArC-H}$); 1625–1573 cm$^{-1}$ ($\upsilon_{ArC=C}$) and 1409–957 cm$^{-1}$ ($\upsilon_{C-F}$). The $^1$H n.m.r. spectrum contained signals at $\delta_H$ (CDCl$_3$) 7.05–7.21, 2-H, 3-H, 5-H and 6-H (dd, J=6.0 Hz and J=6.0 Hz, 4H). The $^{19}$F n.m.r. spectrum had a signal at $\delta_F$ (CDCl$_3$) 120.8, 1-F, 4-F (tt, J=6.0 Hz and J=6.0 Hz).

The mass spectrum produced a molecular ion at m/z 114 and the expected fragmentation pattern for 1,4-difluorobenzene at m/z 94, 88, 81, 75 and 70.

EXAMPLE 8

Diazotization of 2-fluoroaniline in Et$_3$N-3HF

The diazotization of 2-fluoroaniline (2.3 g, 0.02 mol) was performed under the same conditions as those described for 4-fluoroaniline. Addition of sodium nitrite (2.0 g, 0.03 mol) caused the evolution of gas. The clear reaction mixture initially turned yellow and gradually darkened to a red colour. Some tar was formed during addition of sodium nitrite which was partially extracted with diethyl ether (30 cm$^3$). The reaction mixture was poured into water (150 cm$^3$) and extracted with diethyl ether (300 cm$^3$). The combined ether extracts were dried over magnesium sulphate and fractional distillation of the solvent afforded a red oil.

Distillation of the oil at 88–90° C. @ atmospheric pressure afforded 1,2-difluorobenzene (1.32 g, 55.9%) as a clear colourless liquid.

The i.r. spectrum contained major peaks at $\upsilon_{max}$ 3080 cm$^{-1}$ ($\upsilon_{ArC-H}$); 1620–1570 cm$^{-1}$ ($\upsilon_{ArC=H}$) and 1401–900 cm$^{-1}$ ($\upsilon_{C-F}$) and the $^1$H n.m.r. spectrum showed signals at $\delta_H$ (CDCl$_3$) 7.05–7.25 (complex m). The $^{19}$F n.m.r. spectrum had a signal at $\delta_F$ (CDCL$_3$) 138.9, 1-F, 2-F (ddd, J=9.0 Hz, J=9.0 Hz and J=5.5 Hz).

The mass spectrum produced a molecular ion at m/z 114 and the expected fragmentation pattern for 1,2-difluorobenzene at m/z 94, 88, 81, 75, 70 and 63.

EXAMPLE 9

Diazotization of Aniline in Et$_3$N-3HF

A similar approach was used for diazotization of aniline as described in preparation Example 7 except aniline (2.3 g, 0.03 mol) was added over a 30 minute period to Et$_3$N-3HF at 0° C. Addition of sodium nitrite (2.3 g, 0.03 mol) caused the evolution of gas. The reaction mixture turned red in colour, which gradually darkened with the formation of some tar. The contents were allowed to warm to room temperature and ultrasound was applied for a further 20 minutes. The reaction mixture was poured into water (150 cm$^3$) and extracted with diethyl ether (250 cm$^3$). The tarry material was extracted with diethyl ether (20 cm$^3$) and finally washed with water (10 cm$^3$). The combined extracts were dried over magnesium sulphate and fractional evaporation of solvent afforded a brown oil.

Distillation of the oil at 80–81° C. @ atmospheric pressure afforded fluorobenzene (1.30 g, 54.8%) as a clear liquid.

The i.r. spectrum contained major peaks at $\upsilon_{max}$ 3075 cm$^{-1}$ ($\upsilon_{ArC-H}$); 1610–1574 cm$^{-1}$ ($\upsilon_{ArC=H}$) and 1415–911 cm$^{-1}$ ($\upsilon_{C-F}$). The $^1$H n.m.r. spectrum showed signals at $\delta_H$ (CDCl$_3$) 7.05, 2-H and 6-H (t, J=8.5 Hz, further splitting J=1.0 Hz, 2H); 7.13, 4-H (t, J=6.3 Hz, 1H); 7.33, 3-H and 5-H (tdq, J=7.5 Hz, J=7.0 Hz and J=2.0 Hz, 2H). The $^{19}$F n.m.r. spectrum had a signal at $\delta_F$ (CDCl$_3$) 113.5, 1-F (ttd, J=9.1 Hz, J=5.5 Hz and J=1.5 Hz).

The mass spectrum produced a molecular ion at m/z 96 and the expected fragmentation pattern for fluorobenzene at m/z 92, 75, 70 and 63.

EXAMPLE 10

Preparation of 1,2-difluorobenzene in HF/THF with Ultrasound

An FEP container was initially cooled to −78° C. with acetone/Drikold and carefully charged with HF/THF (4:1). 2-Fluoroaniline (5.0 g, 0.05 mol) was added to the HF/THF mixture under vigorous stirring and allowed to warm to −10° C. When the desired temperature was reached the container was transferred to an ultrasonic bath containing an ice-salt water mixture. The container was fitted with a Drikold condenser adapted with a polypropylene filter funnel.

Sodium nitrite (4.95 g, 0.07 mol) was added over 35 minutes under the influence of ultrasound. During the addition an exothermic reaction occurred with the evolution of a brown gas. The ultrasound was applied for a further 1 hour after the complete addition of sodium nitrite at room temperature. The mixture was further heated for 1 hour at 45° C. under the influence of ultrasound. Dediazoniation was complete after 1 hour. The mixture was poured onto iced water (150 cm$^3$). The organic constituents were extracted with dichloromethane (200 cm$^3$×2). The extracts were finally washed with water (100 cm$^3$), stirred with sodium fluoride (2.5 g) and dried with magnesium sulphate for 12 hours.

The solvent was removed by fractional distillation which afforded a red oil. Distillation of the oil @ atmospheric pressure afforded a clear liquid of 1,2-difluorobenzene at 88–91° C. (2.92 g, 56.9%).

The i.r. $^1$H n.m.r., $^{19}$F n.m.r and mass spectrometery results were similar to those from Example 8 which confirmed the formation of 1,2-difluorobenzene. Without ultrasound the yield is only 24%.

EXAMPLE 11

Preparation of 1,4-difluorobenzene in HF/THF with Ultrasound

An FEP container was cooled to −78 ° C. and HF followed by THF was added in a ratio of 4:1. 4-Fluoroaniline (5.0 g, 0.05 mol) was added to the HF/THF under vigorous stirring. After the complete addition the reaction mixture was allowed to warm to −10° C. and fitted with a Drikold condenser. The reaction mixture was placed in an ultrasonic bath containing ice-salt water mixture. Sodium nitrite (4.95 g, 0.07 mol) was added in portions (90 mg) over 1 hour under the influence of ultrasound. The addition caused evolution of a brown gas which became significant after 30 minutes. Ultrasound was applied for a further 1 hour at room temperature and then heated at 45° C. for another 1 hour.

The following work-up was similar to that described in Example 10. Fractional removal of dichloromethane afforded an orange oil. Distillation of the oil @ atmospheric pressure afforded to clear liquid of 1,4-difluorobenzene at 87–88° C. (3.16 g, 62.0%). Without ultrasound, the yield is only 40%.

EXAMPLES 12 AND 13

The addition of BF$_3$-etherate complex has helped to improve the yield of isolated 1,2-difluorobenzene and 1,4difluorobenzene as shown below. -

| Substrate | Product | Yield % | Conditions |
|---|---|---|---|
| 2-fluoroaniline | 1,2-difluorobenzene | 60 | NaNO$_2$, BF$_3$ etherate with ultrasound |
| 4-fluoroaniline | 1,4-difluorobenzene | 68 | NaNO$_2$, BF$_3$ etherate with ultrasound |

The procedures used for these reactions are similar to Examples 10 and 11. 5 cm$^3$ of the BF$_3$ etherate complex were used.

EXAMPLES 14, 15 and 16

Proceeding as in Example 1, the following α-amino acids were converted into the corresponding α-fluoroacids in the stated yields:

| | | |
|---|---|---|
| Example 14 | β-alanine | 50% |
| Example 15 | DL-Valine | 75% |
| Example 16 | L-phenylalanine | 70% |

EXAMPLES 17 TO 22

The reactions were carried out as described in Example 1 except that, in place of the ultrasonic bath, a microwave oven operating at 2.45 GHz with a 720W output, was used. The following amino-compounds were converted into the corresponding fluorocompounds in the stated yields:

| | | |
|---|---|---|
| Example 17 | β-alanine | 65% |
| Example 18 | DL-valine | 60% |
| Example 19 | L-phenylalanine | 69% |
| Example 20 | L-Isoleucine | 57% |
| Example 21 | L-Tyrosine | 40% |
| Example 22 | (+)α-Phenylethylamine | 63% |

What is claimed is:

1. Process for converting a compound containing a primary amino group into a compound containing a fluorine atom in place of said amino group which comprises contacting said amino-group-containing compound with hydrogen fluoride, or with a complex thereof with a base, and a nitrosating reagent at a temperature in the range −20° to +150° C. while subjecting the reagents to the action of ultrasound having a frequency of 10 to 100 kHz and an intensity of at least 20 Watts/cm$^2$ or to the action of microwaves having a frequency of 300 MHz to 3GHz and an intensity between 100 W and 5 kW.

2. Process according to claim 1 wherein the amino-group-containing compound in an aromatic or heteroaromatic primary amine or an α-amino-acid.

3. Process according to claim 1 wherein the amino-group-containing compound is a compound of formula

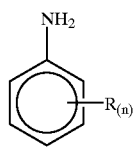

where n is 0, 1, 2 or 3 and the radicals R, which may be the same or different when n is 2 or 3, are each halogen, alkyl of 1 to 4 carbon atoms, alkoxy of 1 to 4 carbon atoms, alkylthio of 1 to 4 carbon atoms, carboxy, alkoxycarbonyl with 1 to 4 carbon atoms in the alkoxy, nitro, cyano or trifluoromethyl.

4. Process according to claim 1 wherein a hydrogen fluoride complex is used in which the base is a secondary or tertiary aliphatic amine, a heterocyclic aromatic amine, or an ether.

5. Process according to claim 4 wherein the said base is trimethylamine, diisopropylamine, pyridine, tetrahydrofuran diethyleneglycol dimethyl ether, 1,3-dioxolane or dioxane.

6. Process according to claim 1 wherein the nitrosating reagent is an alkali metal nitrite or a nitrite ester.

7. Process according to claim 1 wherein the reaction is carried out in the presence of boron trifluoride etherate.

8. Process according to claim 1 wherein the reaction temperature is 0° to 50° C.

* * * * *